United States Patent [19]

von Gentzkow

[11] Patent Number: 4,629,812
[45] Date of Patent: Dec. 16, 1986

[54] METHOD FOR PRODUCING N,N'-BIS-SALICYLOYL HYDRAZINE

[75] Inventor: Wolfgang von Gentzkow, Kleinsendelbach, Fed. Rep. of Germany

[73] Assignee: Siemens Aktiengesellschaft, Munich, Fed. Rep. of Germany

[21] Appl. No.: 294,032

[22] Filed: Aug. 18, 1981

[30] Foreign Application Priority Data

Sep. 4, 1980 [DE] Fed. Rep. of Germany ....... 3033383

[51] Int. Cl.$^4$ ............................................ C07C 103/20
[52] U.S. Cl. .................................... 564/134; 564/136; 564/139; 564/148; 564/150
[58] Field of Search ............... 564/134, 136, 139, 150, 564/148

[56] References Cited

U.S. PATENT DOCUMENTS

| 2,694,072 | 11/1954 | Glahn et al. | 584/138 X |
| 2,711,415 | 6/1955 | Cottle et al. | 564/138 X |
| 2,928,875 | 3/1960 | Martin et al. | 564/148 |
| 3,081,321 | 3/1963 | Young | 564/138 X |
| 4,002,680 | 1/1977 | Brunetti et al. | 564/138 X |

Primary Examiner—Robert V. Hines
Attorney, Agent, or Firm—Kenyon & Kenyon

[57] ABSTRACT

The invention relates to a method for the production of N,N'-bis-salicyloyl hydrazine by a catalytic reaction of salicylic-acid alkyl esters with hydrazine or salicylic-acid hydrazide and has the object to develop such a method in such a manner that not only an N,N'-bis-salicyloyl hydrazine with reduced eye irritation is obtained, but wherein the product is also produced with a high yield and purity. For this purpose, the invention provides that hydrazine or salicylic-acid hydrazide is heated with a 1-to-10 times excess of salicylic-acid alkyl ester in the presence of a halogenide, hydroxide or oxide of boron, aluminum or zinc to temperatures of up to 150° C. The N,N'-bis-salicyloyl hydrazine prepared by the method according to the invention is suitable particularly as an additive to polymers for cable and wire insulation in power and communication engineering.

4 Claims, No Drawings

METHOD FOR PRODUCING N,N'-BIS-SALICYLOYL HYDRAZINE

BACKGROUND OF THE INVENTION

The present invention relates to a method for producing N, N'-bis-salicyloyl hydrazine by catalytic reaction of salicylic acid alkyl esters with hydrazine or salicylic-acid hydrazide.

In the presence of copper, many organic materials, particularly polymers such as polyolefins, but also other polymers such as polyoxymethylene, polyamide and unsaturated polyester resins which currently are in use in electrical engineering for insulating purposes, are subject to accelerated thermo-oxidative aging, which degrades their electrical and mechanical long-term use properties considerably. Especially serious is the damaging effect of copper at elevated temperatures, since the rate of aging of the polymers increases sharply with increasing temperatures.

Cross-linked polyolefins, which are used increasingly as insulating material for cables and wires, particularly are subject to strongly accelerated aging in the presence of copper and must, therefore, be protected effectively against the oxidation-accelerating influence of copper. According to experience, this can be accomplished by inserting a foil as a separating layer between the copper conductor and the insulation, or by using tinned conductors, thereby avoiding direct contact between the copper and the insulation. Such measures, however, are expensive and very cumbersome in production. Thus, for example, if a foil is used as the separating layer, only low production rates are possible, particularly for small conductor cross sections.

Another simple processing approach for obtaining the desired requirements as to quality and thermal stability of polymer materials in contact with copper involves the use of so-called copper deactivators, which inhibit the oxidation-accelerating effect of copper even at elevated temperatures. Stabilizing polymer materials by copper deactivators is, therefore, a cost-effective measure.

It is known from U.S. Pat. No. 3,849,492 to use copper deactivators of the N, N'-bis-salicyloyl hydrazine type. Multiple alkyl or alkoxy-substituted derivatives of the base compound allegedly have been found to be particularly effective for stabilizing polyolefins against the damaging effect of copper and other transition metals.

From German Pat. No. 27 03 558 (column 2, lines 49 to 65) and the corresponding South-African Pat. No. 78/0086 it is known that for a permanent stabilization of polymers in contact with copper, a combination of N, N'-bis-salicyloyl-hydrazine as the metal deactivator and oligomeric 2,2,4-trimethyl-1,2-dihydroquinoline as an oxidation inhibitor is advantageous. This stabilizing combination has been found to be particularly effective also for stabilizing cross-linked polyolefins. The high effectiveness of N, N'-bis-salicyloyl hydrazine as a metal deactivator has been determined in extensive investigations on model conductors and by aging tests on commercial products.

In the mentioned stabilizer combination, the metal deactivator employed was a commercial product which was obtained directly by reaction of salicylic-acid hydrazide with salicylic acid, adding thionyl chloride and pyridine in chlorobenzene and, after purification by washing with alcohol, was present in a degree of purity of 99% see British Pat. No. 1,398,360).

Mixing a metal deactivator of the type mentioned (as well as further additives) into a polymer material such as, for example, a polyolefin for cable and wire insulation, is accomplished on a technical scale by conventional mixing processes. In cable and wire technology, so-called concentrates consisting of a metal deactivator or other additives and polymer material, preferably are prepared first and then are processed by mixing them into further polymer material to form insulating mixtures with the desired concentrations of metal deactivator and the further additives. In the preparation of the concentrates with the metal deactivator prepared in this manner on a commercial scale, it has been found that eye irritations or eye damage occurs in persons engaged therein.

To determine the cause of eye irritations or eye damage, tests with rabbits were made. Since it must be assumed that the copper deactivator can get into the eye in solid form, for example, as dust during the technical processing, the solid substance was placed, repeatedly, directly into the eye of the test animals at relatively short time intervals, for example, daily, and the changes in the eye were observed over an extended period of time. As a result of these tests, it was found that the eye irritations and eye damage are due to the N, N'-bis-salicyloyl hydrazine itself or to small quantities of impurities due to the manufacturing process.

From U.S. patent application Ser. No. 173,409, filed July 29, 1980 and now U.S. Pat. No. 4,446,260, it can be seen that eye irritations or eye damage can be considerably reduced if an N, N'-bis-salicyloyl-hydrazine is used which is obtained by reaction of salicylic-acid alkyl esters with hydrazine or salicylic acid hydrazide. This reaction can occur in the presence of nucleophilic and/or electrophilic catalysts, nucleophilic catalysis being preferred. Particular catalysts include primary, secondary or tertiary amines as well as amino group-containing compounds such as nitrogen-containing heterocycles, amides and hydrazines, or the ammonium salts of these amines and amino group-containing compounds with inorganic or organic acids.

A disadvantage of the reaction utilizing nucleophilic catalysts of the type mentioned above, however, is that the product is produced in a form which is colored yellowish by additives, therefore requiring further processing, such as by recrystallization, for purification. On the other hand, attempting to conduct the reaction in the absence of catalysts, or with protonated acids as catalysts, results in very low yields of product.

SUMMARY OF THE INVENTION

It is an object of the present invention to develop the method of the type mentioned at the outset in such a manner that not only an N, N'-bis-salicyloyl-hydrazine with reduced eye irritation is obtained but also that the product is produced with high yield and purity.

According to the present invention, this and other objects are achieved by heating hydrazine or salicylic-acid hydrazide with a 1- to 10-times excess of salicylic-acid alkyl ester in the presence of halogenides, hydroxides or oxides of boron, aluminum or zinc at temperatures of up to 150° C.

It has been found, surprisingly, that in the reaction of hydrazine or salicylic-acid hydrazide with salicylic-acid alkyl esters, an N,N'-bis-salicyloyl hydrazine is produced with high yields and high purity if one proceeds without solvent with an excess of liquid salicylic-acid alkyl ester at temperatures below 150° C., and if an electrophilic catalyst of the type mentioned above is used. The catalyst concentrations required for a fast reaction are preferably between about 0.01 and 5% by weight, referred to the total weight of the reaction mixture, depending on the effectiveness.

If aluminum oxide or aluminum oxide hydrates are used as the catalyst, the catalyst concentration is important only with respect to the catalyst surface required for heterogeneous catalysis. If a large specific catalyst surface is available, very small amounts of catalyst can bring about high yields. However, the use of high purity aluminum oxide or aluminum oxide hydrates is important because even small amounts of heavy-metal impurities lead to coloring of the N, N'-bis-salicyloyl hydrazine. To make possible a simple separation of the product precipitated during the reaction from the solid catalyst, it has furthermore proved useful to generate the aluminum oxide through oxidation as a coating on aluminum parts in the reactor (inside wall or stirrer) or to fasten the catalyst in the reactor in the form of anodized aluminum foils.

With the method according to the present invention, it has been found to be advantageous to use salicylic-acid alkyl esters which are liquid at room temperature. Therefore, salicylic-acid esters preferably used in this method are those wherein the alkyl radical has 1 to 5 carbon atoms.

A particularly pure and colorless N, N'-bis-salicyloyl-hydrazine is obtained with a yield practically equal to the theoretical value if, starting from salicylic-acid methyl ester, one works with an excess thereof (300 to 350% of the stoichiometrically required amount) at temperatures of maximally 145° C., and boric acid is used as a catalyst in a concentration of 0.5 to 1%, referred to the total weight of the reaction mixture. The use of boric acid, i.e., $H_3BO_3$ (or $B(OH)_3$), has been found to be advantageous, because boric acid is volatilized during the reaction in the form of boric-acid trimethyl ester and, in this manner, a particularly pure product is obtained which is free of catalyst residue.

A particularly advantageous variant of the catalysis with boric acid is the use of boron trioxide, $B_2O_3$. Boron trioxide is reacted during the reaction cycle with small amounts of water to form boric acid. This ensures a highly controlled course of the overall reaction and particularly high yields. If one starts in the production of N, N'-bis-salicyloyl-hydrazine with salicylic-acid methyl ester and hydrazine hydrate, and the catalysis is performed with $B_2O_2$ or $B(OH)_3$ or $Al_2O_3$, then the synthesis becomes very simple as far as equipment is concerned ("single-pot reaction"), can be carried out easily on a large technical scale, and is extremely inexpensive if the unconverted reactants are redistilled.

In addition, the N, N'-bis-salicyloyl hydrazine prepared in accordance with the method of the present invention has the lowest eye-irritating or eye-damaging effect determined to date for such compounds, which could be explained by the high purity and the favorable crystal form (rounded corners and edges) of the product obtained during the reaction.

The product synthesized according to the invention is used as a copper deactivator to particular advantage if mixed with conventional phenolic or aminic oxidation inhibitors for stabilizing organic materials, particularly plastics and plastic precursor products, to counteract oxidative decomposition. A particularly synergistic effect is obtained in a mixture with oligomeric 2,2,4-trimethyl-1,2-dihydroquinoline. The processing of the metal deactivator synthesized in accordance with the present invention for stabilizing plastics can be accomplished using the customary mixing techniques, for example, via concentrates, but also by direct dosing of a metal deactivator which is adjusted for more compatible processing by suitable liquid additives.

With the copper deactivator synthesized according to the present invention, cross-linked and non-cross-linked thermoplastics (such as cross-linked and non-cross-linked polyolefins) and elastomers, as well as reaction resins in the hardened and unhardened state, can be protected advantageously against detrimental catalytic influences of copper. Polymers which contain the metal deactivator according to the present invention can be used to particular advantage as cable and wire insulation in power engineering and communication engineering. In addition, the copper deactivator synthesized according to the present invention also can be used for stabilizing polymer materials, insulating oils and lubricating grease, which are in contact with copper or contain copper ions. Such materials are employed particularly in electrical engineering.

DETAILED DESCRIPTION OF THE INVENTION

The present invention will now be explained in greater detail with the aid of the following examples.

EXAMPLE 1

152 parts by weight salicylic-acid hydrazide are heated with 380 parts salicylic-acid methyl ester and a corresponding quantity of catalyst (see Table 1) to a temperature of about 140° to 145° C. while stirring. Methanol produced during the reaction is distilled off via a column. Ater about 1 hour, the reaction mixture starts to become viscous due to the precipitating N, N'-bis-salicyloyl hydrazine. After 2 hours, the reaction is finished. The then very viscous reaction liquid is cooled down to 70° C., reacted with the same volume of alcohol (methanol or ethanol) and stirred for about 30 minutes at 60° to 70° C. After it has cooled down, it is suctioned off, washed with alcohol and dried in a vacuum. A pure-white product with a decomposition range of 305° to 310° C. is obtained. The yields are given in Table 1.

EXAMPLE 2

50 parts by weight hydrazine hydrate are boiled with 532 parts by weight salicylic-acid methyl ester for 2 hours while refluxing and stirring. After about 1 hour, salicylic-acid hydrazide begins to precipitate. After 2 hours, water and methanol formed are distilled off via a column and a corresponding quantity of catalyst is added to the reaction mixture and the mixture heated to a temperature of about 140° to 145° C. while stirring (see Table 1). In the process, a large part of the previously precipitated salicylic-acid hydrazide is dissolved again. During the further course of the reaction, methanol formed is distilled-off continuously via a column. After about 1 hour, the reaction mixture begins to become viscous by precipitated N, N'-bis-salicyloyl hydrazine. After about 2 hours, the reaction is completed. The then very viscous reaction mixture is cooled off to 70° C. and the same volume of alcohol (methanol or ethanol) is added and is stirred for about 30 minutes at 60° to 70° C. After cooling, it is suctioned off, washed with alcohol and dried in a vacuum. A pure-white product with a decomposition range of 305° to 310° C. is obtained. The yields are given in Table 1.

TABLE 1

| Catalyst | Amount (Parts by Weight) | Method as per Example | Yield % |
|---|---|---|---|
| $BCl_3$ | 12* | 2 | 66** |
| $BF_3.(C_2H_5)_2O$ | 14 | 2 | 62** |
| $B(OH)_3$ | 6 | 1 or 2 | 93 and 88, resp. |
| $B_2O_3$ | 3 | 1 or 2 | 94 and 93 |
| $Al_2O_3$ (granular) | 10 | 1 or 2 | 84** and 78** |
| $Al_2O_3.3H_2O$ (granular) | 15 | 1 or 2 | 82** and 74** |
| $ZnCl_2$ | 14 | 2 | 60 |

*Calculated value from the quantity introduced in gaseous form.
**The yields can be increased by lengthening the reaction time.

EXAMPLE 3

152 parts by weight salicylic-acid hydrazide are heated with 380 parts by weight salicylic-acid methyl ester to a temperature of about 140° to 145° C. in a vessel while stirring with a large-area anodized aluminum stirrer. After about 2 hours, the reaction mixture begins to become viscous by precipitated N, N'-bis-salicyloyl hydrazine. After 3 hours, the viscous reaction mixture is cooled down to 70° C., reacted with the same volume alcohol (methanol or ethanol) and is stirred for about 30 minutes at 60° to 70° C. After cooling, it is suctioned off, washed with alcohol and dried in a vacuum. With a yield of about 80% referred to salicylic-acid hydrazide, a pure-white product with a decomposition range of 305° to 310° C. is obtained. The yield can be increased further by making the catalyst surface larger or by increasing the reaction time.

EXAMPLE 4

If the reaction according to Example 2 is carried out in accordance with Example 3, i.e., using a large-area anodized aluminum stirrer, a pure-white product with a decomposition range of 305° to 310° C. is obtained with a yield of 76%. The yield can be increased still further by increasing the catalyst area or by increasing the reaction time.

A test of the eye-irritating or eye-damaging effect of N, N'-bis-salicyloyl hydrazine prepared by the method according to the present invention was carried out in accordance with the testing method already mentioned. Per test series, 0.1 g of substance was applied to 6 rabbits daily for 5 days in the conjunctiva sack of the right eye. Three of the 6 test animals of a test series had the conjunctiva sack rinsed a short time after the application, with physiological salt solution, paying attention to complete removal of the substance. The remaining 3 test animals of the same test series were not treated further.

In the rabbits, the eyes of which were not rinsed out after the application of N, N'-bis-salicyloyl hydrazine, only a temporary relatively slight reddening of the conjunctiva and a slight hazy cloudiness of the cornea took place. In the rabbits whose eyes were rinsed after the treatment, no damage to the eyes could be proven except for a temporary slight irritation during the application period.

What is claimed is:

1. In a method for producing N, N'-bis-salicyloyl hydrazine by a catalytic reaction of salicylic-acid alkyl esters with hydrazine or salicylic-acid hydrazide, the improvement comprising heating said hydrazine or salicylic-acid hydrazide to temperatures of up to about 150° C. with a 1- to 10-times excess of salicylic-acid alkyl ester in the presence of a halogenide, hydroxide or oxide of boron, aluminum or zinc.

2. The method according to claim 1 wherein said catalyst is employed in an amount of 0.01 to 5% by weight, referred to the total weight of the reaction mixture.

3. The method according to claim 2, wherein a 2-to 3-times excess of salicylic-acid alkyl ester is used.

4. The method according to claim 1 wherein said catalyst is boric acid $B(OH)_3$ or boron trioxide $B_2O_3$.

* * * * *